United States Patent
Ingmanson et al.

(10) Patent No.: US 10,265,090 B2
(45) Date of Patent: Apr. 23, 2019

(54) HAND HELD ELECTROMECHANICAL SURGICAL SYSTEM INCLUDING BATTERY COMPARTMENT DIAGNOSTIC DISPLAY

(71) Applicant: Covidien LP, Mansfield, MA (US)

(72) Inventors: Michael D. Ingmanson, Stratford, CT (US); Kelly Valentine, Newington, CT (US); Elizabeth Hufnagel, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1136 days.

(21) Appl. No.: 14/143,371

(22) Filed: Dec. 30, 2013

(65) Prior Publication Data

US 2014/0200561 A1 Jul. 17, 2014

Related U.S. Application Data

(60) Provisional application No. 61/753,110, filed on Jan. 16, 2013.

(51) Int. Cl.
*H01M 2/10* (2006.01)
*H01M 6/50* (2006.01)
(Continued)

(52) U.S. Cl.
CPC ........ *A61B 17/29* (2013.01); *A61B 17/07207* (2013.01); *A61B 17/1622* (2013.01);
(Continued)

(58) Field of Classification Search
CPC .................. H01M 6/5061; A61B 2017/00734
See application file for complete search history.

(56) References Cited

U.S. PATENT DOCUMENTS 5,057,383 A 10/1991 Sokira
5,418,086 A 5/1995 Bailey
(Continued)

FOREIGN PATENT DOCUMENTS

CN 101401736 A 4/2009
EP 2090256 8/2009
(Continued)

OTHER PUBLICATIONS

Extended European Search Report corresponding to EP 14 15 1221.0, completed Apr. 22, 2014 and dated May 2, 2014; (9 pp).
(Continued)

*Primary Examiner* — Christopher Koharski
*Assistant Examiner* — Amanda L Steinberg

(57) ABSTRACT

An electromechanical surgical system is provided and includes a hand-held surgical device. The surgical device includes a device housing defining a connecting portion for selectively connecting with an adapter assembly, the housing being configured to removably receive a battery therein; at least one drive motor supported in the device housing and being configured to rotate a drive shaft; and a circuit board disposed within the housing for controlling power delivered from a battery to the motor. The system includes a battery configured for disposition in the device housing, the battery being capable of powering the at least one drive motor, the battery including at least one display. The device housing is configured such that the at least one display of the battery is visible therethrough.

18 Claims, 6 Drawing Sheets

(51) Int. Cl.

| | | |
|---|---|---|
| *A61B 17/00* | (2006.01) | |
| *A61B 17/16* | (2006.01) | |
| *A61B 17/29* | (2006.01) | |
| *A61B 34/00* | (2016.01) | |
| *A61B 34/20* | (2016.01) | |
| *A61B 90/00* | (2016.01) | |
| *G06F 19/00* | (2018.01) | |
| *H01M 10/42* | (2006.01) | |
| *H01M 10/48* | (2006.01) | |
| *H02K 11/00* | (2016.01) | |
| *H02K 11/33* | (2016.01) | |
| *A61B 17/072* | (2006.01) | |

(52) U.S. Cl.
CPC ............. *A61B 34/74* (2016.02); *G06F 19/00* (2013.01); *H01M 2/1066* (2013.01); *H01M 6/505* (2013.01); *H01M 10/425* (2013.01); *H01M 10/488* (2013.01); *A61B 2017/00017* (2013.01); *A61B 2017/00039* (2013.01); *A61B 2017/0046* (2013.01); *A61B 2017/00075* (2013.01); *A61B 2017/00115* (2013.01); *A61B 2017/00199* (2013.01); *A61B 2017/00398* (2013.01); *A61B 2017/00464* (2013.01); *A61B 2017/00473* (2013.01); *A61B 2017/00477* (2013.01); *A61B 2017/00734* (2013.01); *A61B 2017/00902* (2013.01); *A61B 2017/00907* (2013.01); *A61B 2017/2903* (2013.01); *A61B 2034/2048* (2016.02); *A61B 2090/0803* (2016.02); *A61B 2090/0808* (2016.02); *A61B 2090/0813* (2016.02); *H01M 2220/30* (2013.01); *H02K 11/0094* (2013.01); *H02K 11/33* (2016.01)

(56) References Cited

U.S. PATENT DOCUMENTS

| | | | |
|---|---|---|---|
| 5,510,205 | A | 4/1996 | Ozer |
| 7,064,522 | B2 | 6/2006 | Nawa |
| 7,819,896 | B2 | 10/2010 | Racenet |
| 2005/0020909 | A1 | 1/2005 | Moctezuma de la Barrera et al. |
| 2005/0026643 | A1* | 2/2005 | White .................. B23Q 1/0009 455/550.1 |
| 2006/0173290 | A1 | 8/2006 | Lavallee |
| 2006/0206100 | A1 | 9/2006 | Eskridge et al. |
| 2008/0245371 | A1* | 10/2008 | Gruber .................. A61B 1/303 128/831 |
| 2009/0289805 | A1* | 11/2009 | Patrick ................. H01M 10/488 340/636.11 |
| 2010/0100081 | A1* | 4/2010 | Tuma ..................... A61B 17/00 606/1 |
| 2011/0074594 | A1* | 3/2011 | Dycus ..................... H01M 2/34 340/679 |
| 2011/0125138 | A1* | 5/2011 | Malinouskas ........ A61B 17/068 606/1 |
| 2011/0208093 | A1* | 8/2011 | Gross ................... A61B 5/4528 600/587 |
| 2012/0089131 | A1 | 4/2012 | Zemlok et al. |
| 2012/0253329 | A1 | 10/2012 | Zemlok |

FOREIGN PATENT DOCUMENTS

| | | |
|---|---|---|
| EP | 2124287 | 11/2009 |
| JP | 1243646 | 9/1989 |

OTHER PUBLICATIONS

BrainlabCorporate: "Dash—Computer Assisted Joint Replacement with the iPod Touch", URL:http://www.youtube.com/watch?v=pE3xce20Bi8; Feb. 17, 2011, p. 1, XP054975144.

Apple Inc.: "iPod Touch User Guide for iOS 4.3 Software", URL:http://manuals.info.apple.com/en_US/iPod_touch_iOS4_User_Guide.pdf; Jul. 12, 2012, pp. 1-230, XP055113771.

Partial European Search Report dated Mar. 15, 2016 in corresponding European Patent Application No. 15 19 2309, 11 pages.

Japanese Office Action corresponding to counterpart Chinese Appln. No. CN 2014-005750 dated Sep. 15, 2017.

Chinese Second Office Action corresponding to counterpart Chinese Application No. CN 2014100211977 dated Aug. 22, 2017.

Japanese Final Office Action corresponding to counterpart Japanese Patent Appln. No. JP 2014-005750 dated Dec. 25, 2017.

Chinese Office Action dated Dec. 26, 2016 in corresponding Chinese Patent Application No. 201410021197.7 together with English translation, 20 pages.

\* cited by examiner

HAND HELD ELECTROMECHANICAL SURGICAL SYSTEM INCLUDING BATTERY COMPARTMENT DIAGNOSTIC DISPLAY

CROSS-REFERENCE TO RELATED APPLICATIONS

This application claims the benefit of and priority to U.S. Provisional Patent Application No. 61/753,110, filed Jan. 16, 2013, the entire disclosure of which is incorporated by reference herein

BACKGROUND

1. Technical Field

The present disclosure relates to surgical devices and/or systems and their methods of use. More specifically, the present disclosure relates to hand-held, electromechanical surgical devices and/or systems for clamping, cutting and/or stapling tissue.

2. Background of Related Art

A number of surgical device manufacturers have developed product lines with proprietary drive systems for operating and/or manipulating electromechanical surgical devices. In many instances the electromechanical surgical devices include a reusable handle assembly, and disposable or single use loading units. The loading units are selectively connected to the handle assembly prior to use and then disconnected from the handle assembly following use in order to be disposed of, while the handle assembly is sterilized or autoclaved for re-use.

Many of these electromechanical surgical devices include complex drive components that utilize a variety of user interfaces that accept user inputs (e.g., controls) for controlling the devices as well as provide feedback to the user, typically via a sequence of lights or the like (i.e., LED's). However, due to the use of autoclaving to sterilize these electromechanical surgical devices, many traditional communication methods are not useable or integrated into the electromechanical surgical devices, namely, LCD screens, speakers, etc.

Accordingly, a need continues to exist for electromechanical surgical apparatus, devices and/or systems having improved user interfaces.

SUMMARY

The present disclosure relates to hand-held, electromechanical surgical devices and/or systems for clamping, cutting and/or stapling tissue.

According to an aspect of the present disclosure, an electromechanical surgical system is provided and comprises a hand-held surgical device, including a device housing defining a connecting portion for selectively connecting with an adapter assembly, the housing being configured to removably receive a battery therein; at least one drive motor supported in the device housing and being configured to rotate a drive shaft; and a circuit board disposed within the housing for controlling power delivered from a battery to the motor. The surgical system further comprises a battery configured for disposition in the device housing, the battery being capable of powering the at least one drive motor, the battery including at least one display. The device housing is configured such that the at least one display of the battery is visible therethrough.

At least a portion of the device housing may be transparent. The display of the battery may be visible through the transparent portion of the device housing when the battery is received in the device housing.

A door may be supported on the device housing. The door may have an open position for permitting insertion of the battery into the device housing and a closed position for retaining the battery in the device housing. At least a portion of the door may be transparent. The display of the battery may be visible through the transparent portion of the door when the battery is received in the device housing.

The battery may include multiple displays. Each of the displays of the battery may be visible through the device housing.

At least a portion of the device housing may define a window. The display of the battery may be visible through the window of the device housing when the battery is received in the device housing.

The door may define a window, and wherein the display of the battery may be visible through the window of the door when the battery is received in the device housing.

The device housing may include multiple windows, and wherein each of the displays of the battery may be visible through a respective window of the device housing.

At least one of the surgical device and the battery may include an orientation device configured to change an orientation of an image displayed on the at least one display depending on a particular orientation of the surgical device. The orientation device may include at least one of a linear acceleration sensor, a rotational acceleration sensor, a magnetometer, a linear gyroscope and a rotational gyroscope.

At least one of the displays of the battery may display at least one of potential failures of the surgical device, procedural steps for resolving the potential failures, autoclaving counts for the surgical device, end of life counts for the surgical device, features of an internal software EEProm, and battery life.

The battery may include a speaker integrally formed therewith.

The electromechanical surgical system may further comprise an end effector configured to perform at least one function, the end effector including at least one axially translatable drive member; and an adapter assembly for selectively interconnecting the end effector and the surgical device.

The adapter assembly may include an adapter housing configured and adapted for selective connection to the connecting portion of the surgical device and to be in operative communication with each of the at least one rotatable drive shaft of the surgical device; an outer tube having a proximal end supported by the adapter housing and a distal end configured and adapted for connection with the end effector, wherein the distal end of the outer tube is in operative communication with each of the at least one axially translatable drive member of the end effector; at least one drive converter assembly for interconnecting a respective one of the at least one rotatable drive shaft of the surgical device and one of the at least one axially translatable drive member of the end effector, wherein the at least one drive converter assembly includes a first end that is connectable to a drive shaft of the surgical device and a second end that is connectable to the at least one axially translatable drive member of the end effector, wherein the at least one drive converter assembly converts and transmits a rotation of the rotatable drive shaft of the surgical device to an axial translation of the at least one axially translatable drive member of the end effector.

At least one of the displays of the battery may display at least one of potential failures of at least one of the battery, the surgical device, the adapter and the end effector; procedural steps for resolving the potential failures; autoclaving counts for at least one of the surgical device, the adapter and the end effector; end of life counts for at least one of the battery, the surgical device, the adapter and the end effector; features of an internal software EEProm of the surgical device, and battery life.

According to another aspect of the present disclosure, a battery for use in a hand-held electromechanical surgical device is provided. The battery comprises a primary source of energy for energizing the hand-held electromechanical surgical device; and at least one display integral therewith for displaying a parameter of at least one of the battery and the surgical device.

The battery may be configured to display at least one of potential failures of at least one of the battery and the surgical device; procedural steps for resolving the potential failures; end of life counts for at least one of the battery and the surgical device; features of an internal software EEProm of the surgical device.

The battery may include a secondary source of energy for energizing each display.

The battery may include multiple displays. The battery may include a display provided in at least one of a rear wall, a first side wall, a second side wall and a bottom wall thereof.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
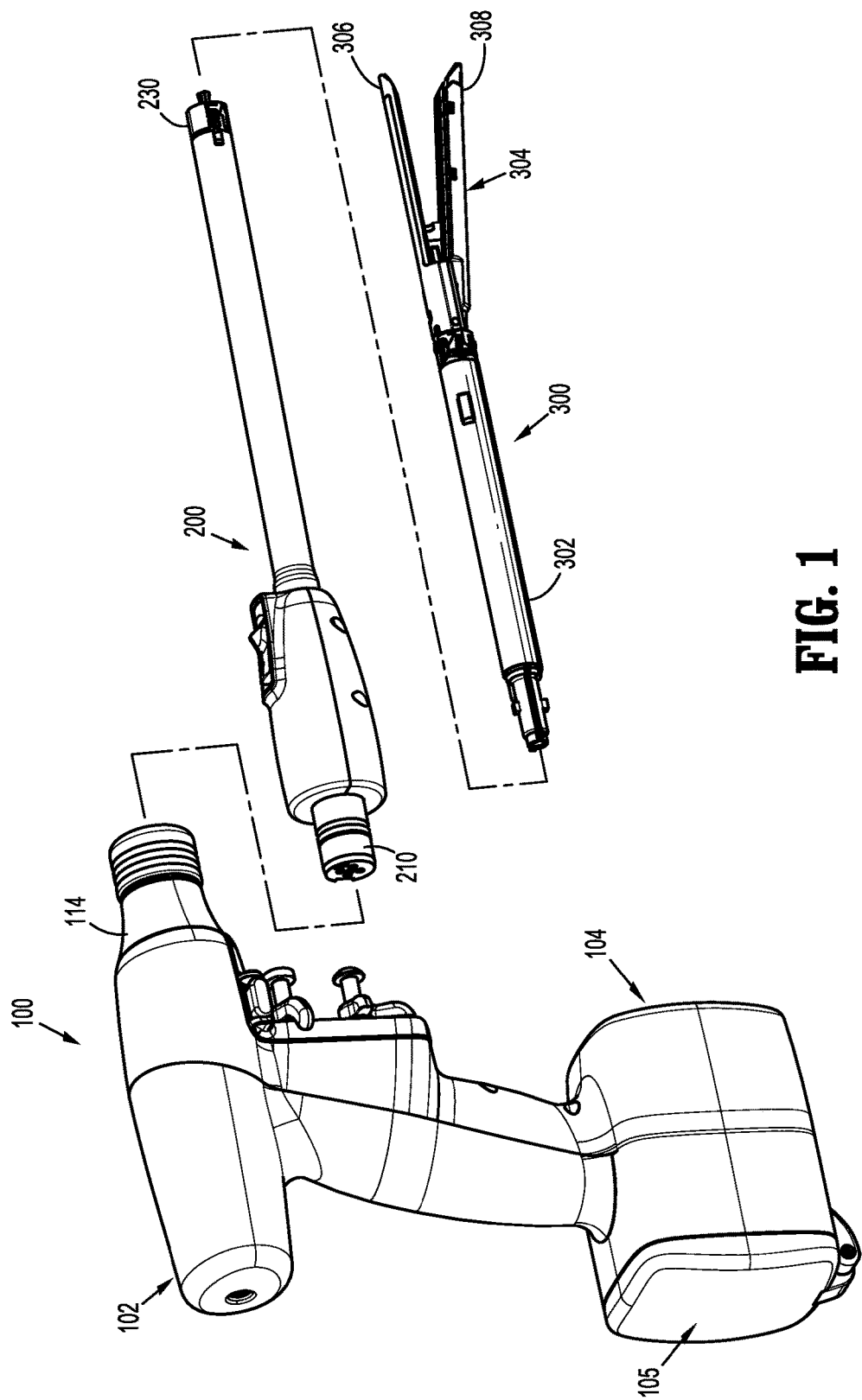
FIG. 1 is a perspective view, with parts separated, of a surgical device and adapter, in accordance with an embodiment of the present disclosure, illustrating a connection thereof with an end effector.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered hand held electromechanical device configured for selective attachment thereto of a plurality of different end effectors that are each configured for actuation and manipulation by the powered hand held electromechanical surgical device.

As illustrated in FIG. 1, surgical device 100 is configured for selective connection with an adapter 200, and, in turn, adapter 200 is configured for selective connection with an end effector or single use loading unit 300.

Figure 2:
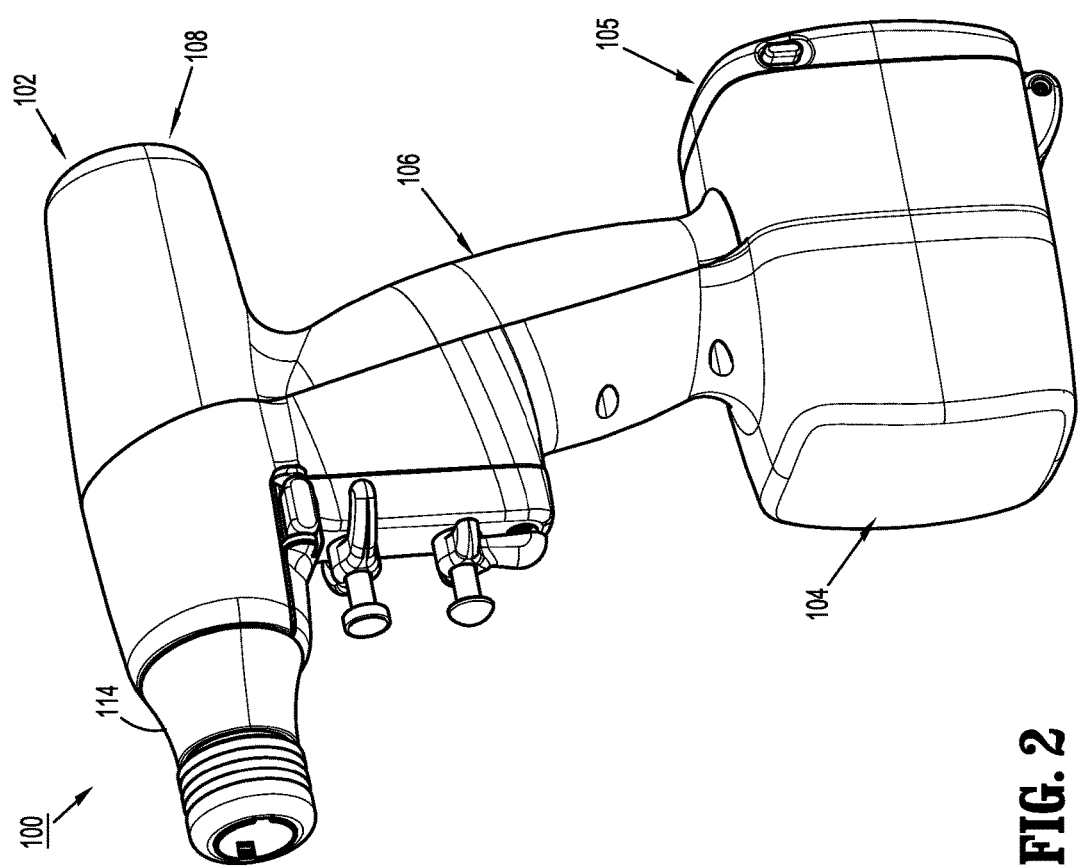
FIG. 2 is a perspective view of the surgical device of FIG. 1.
Figure 3:
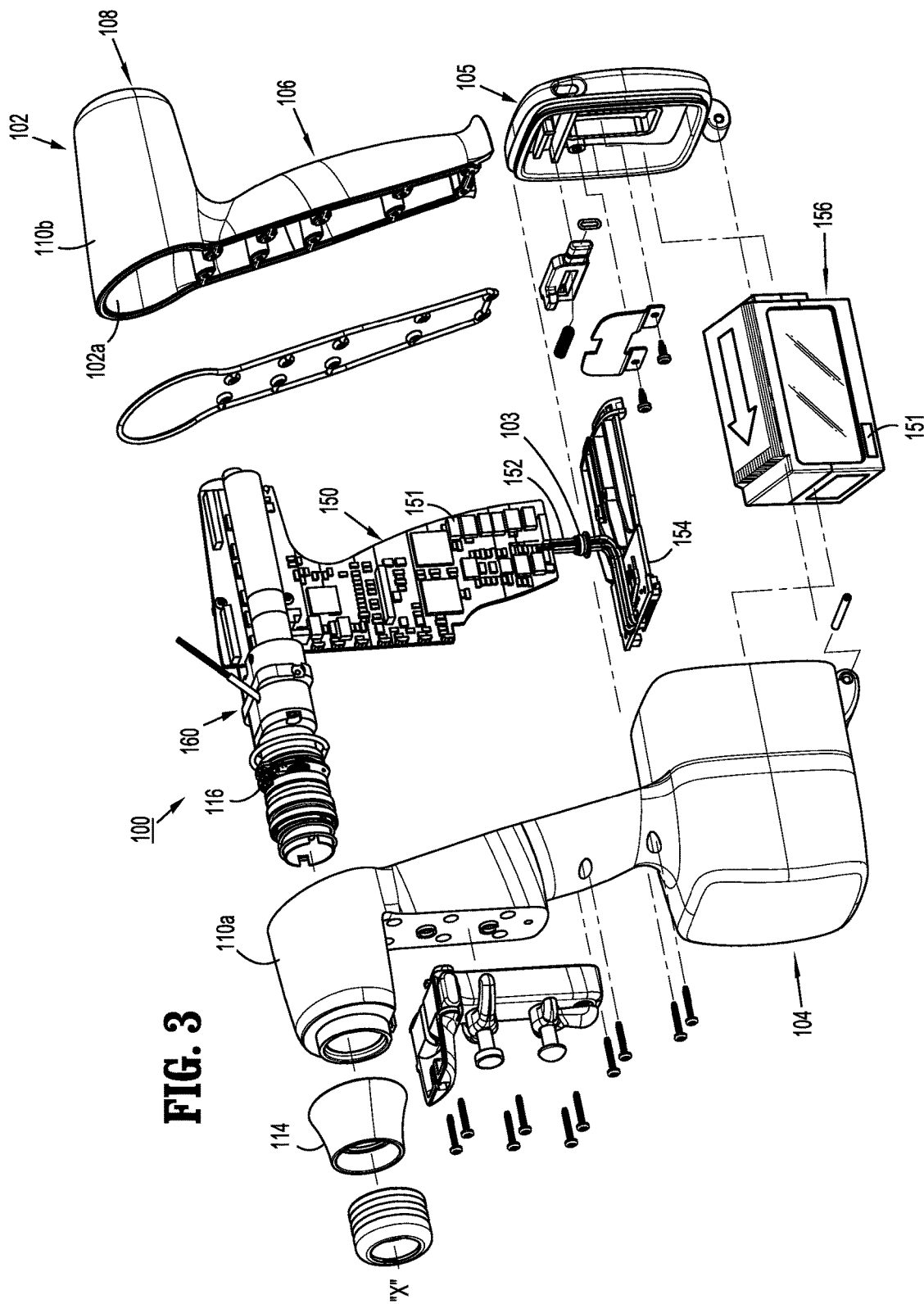
FIG. 3 is a perspective view, with parts separated, of the surgical device of FIGS. 1 and 2.

As illustrated in FIGS. 1-3, surgical device 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 is situated.

Distal and proximal half-sections 110a, 110b are divided along a plane that traverses a longitudinal axis "X" of upper housing portion 108, as seen in FIG. 1.

Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical device 100, as will be set forth in additional detail below.

Lower housing portion 104 of surgical device 100 defines an aperture (not shown) formed in an upper surface thereof and which is located beneath or within intermediate housing portion 106. The aperture of lower housing portion 104 provides a passage through which wires 152 pass to electrically interconnect electrical components (i.e., a battery 156, as illustrated in FIGS. 4A and 4B, a circuit board 154, as illustrated in FIG. 3, etc.) situated in lower housing portion 104 with electrical components (circuit board 150, drive mechanism 160, etc.) situated in intermediate housing portion 106 and/or upper housing portion 108.

Handle housing 102 includes a gasket 103 disposed within the aperture of lower housing portion 104 (not shown) thereby plugging or sealing the aperture of lower housing portion 104 while allowing wires 152 to pass therethrough. Gasket 103 functions to establish an air-tight seal between lower housing portion 106 and intermediate housing portion 108 such that circuit board 150 and drive mechanism 160 are protected from sterilization and/or cleaning procedures.

As shown in FIG. 3, lower housing portion 104 of handle housing 102 provides a housing in which a rechargeable battery 156, is removably situated. Battery 156 is configured to supply power to any of the electrical components of surgical device 100. Lower housing portion 104 defines a cavity (not shown) into which battery 156 is inserted. Lower housing portion 104 includes a door 105 pivotally connected thereto for closing cavity of lower housing portion 104 and retaining battery 156 therein.

Figure 4A:
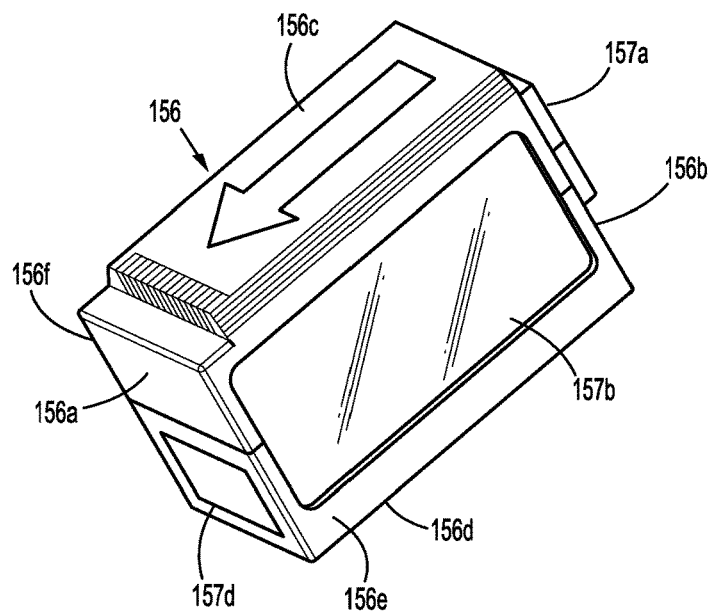
FIG. 4A is a front, perspective view of a battery for use in the surgical device of FIGS. 1-3.
Figure 4B:
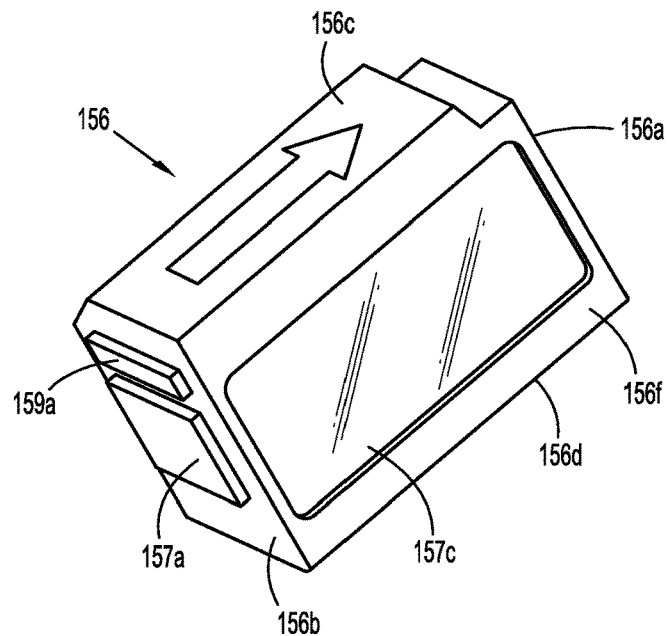
FIG. 4B is a rear, perspective view of the battery of FIG. 4A.

Turning now to FIGS. 4A and 4B, battery 156 includes a front wall 156a, a rear wall 156b, a top wall 156c, a bottom wall 156d, a right wall 156e, and a left wall 156f. In accordance with the present disclosure, battery 156 includes a first display 157a supported therein and visible through rear wall 156b. It is contemplated, as seen in FIGS. 4A and 4B, that battery 156 may include a second display 157b supported therein and visible through right wall 156e, a third first display 157c supported therein and visible through left wall 156f and/or a fourth display 157d supported therein and visible through front wall 156a. Although not shown, it is contemplated that a display may be provided in bottom wall 156d or any outer wall or surface of battery 156.

Each display 157a-157d may include, and is not limited to light emitting diodes (LED's), liquid crystal displays (LCD's) and the like. Displays 157a-157d, as will be described in greater detail below, may provide a user with visual indications and/or notifications prior to, during and/or following a surgical procedure preformed with surgical device 100.

In an embodiment, it is contemplated that battery 156, as will be described in greater detail below, may include a speaker 159a supported in rear wall 156b. Speaker 159a may provide a user with audible indications and/or notifications prior to, during and/or following a surgical procedure preformed with surgical device 100.

Figure 5A:
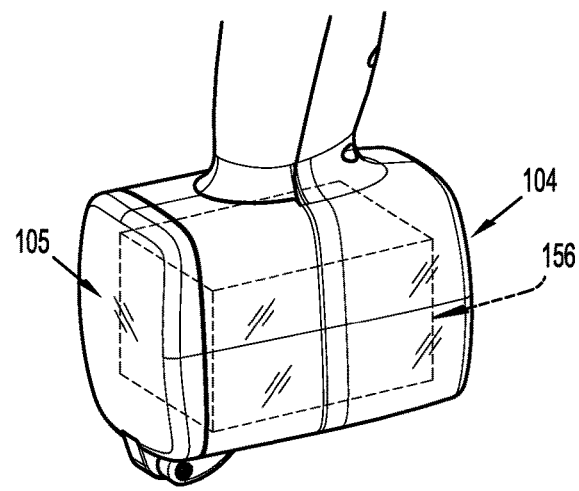
FIG. 5A is a rear, perspective view of a lower portion of a surgical device according to an embodiment of the present disclosure.
Figure 5B:
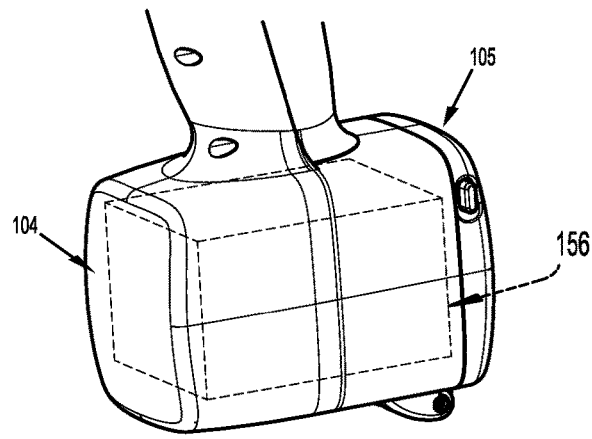
FIG. 5B is a front, perspective view of the lower portion of FIG. 5A.

Turning now to FIGS. 5A and 5B, in accordance with an embodiment of the present disclosure, surgical device 100 may include a lower housing portion 104 and/or a door 105 fabricated from a transparent or translucent material. By fabricating lower housing portion 104 and/or door 105 from a transparent or translucent material, the displays 157a=157d of battery 156 may be visible therethrough by an end user (i.e., surgeon, nurse, etc.).

Exemplary transparent or translucent materials for lower housing portion 104 and/or door 105 include and are not limited to polycarbonate, polytetrafluoroethylene (PTFE), fluorinated ethylene propylene (FEP), Ethylene chlorotrifluoroethylene (ECTFE), polychlorotrifluoroethylene (PCTFE), acrylics, plastics etc. which are resistant to the sterilizing and/or autoclaving procedures which surgical device 100 is subjected to following each surgical procedure. In particular, the materials for lower housing portion 104 and/or door 105 should be resistant to dulling, discoloring or opaquing overtime as surgical device 100 is subjected to the sterilizing and/or autoclaving procedures.

Figure 6A:
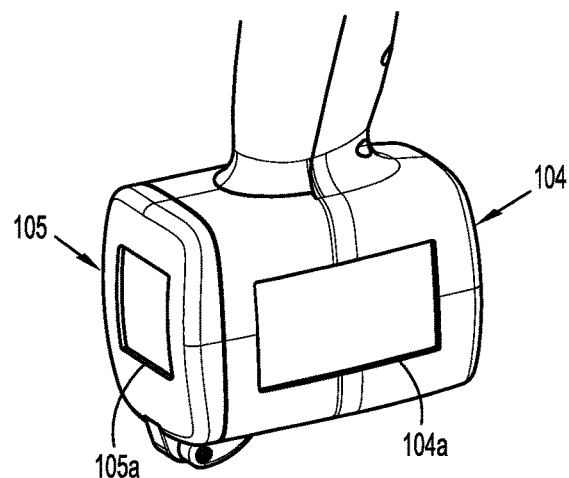
FIG. 6A is a rear, perspective view of a lower portion of a surgical device according to another embodiment of the present disclosure.
Figure 6B:
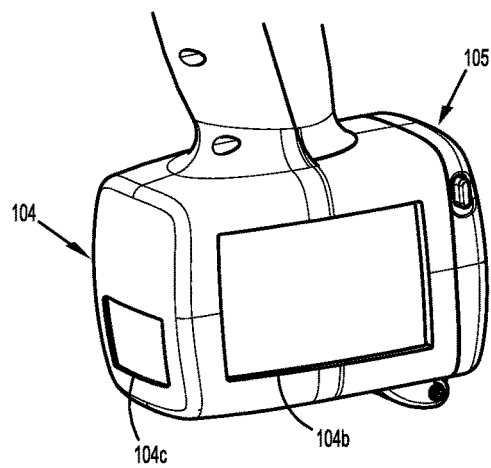
FIG. 6B is a front, perspective view of the lower portion of FIG. 6A.

Turning now to FIGS. 6A and 6B, in an alternate embodiment, lower housing portion 104 may include a first window 104a formed in a side wall thereof, a second window 104b formed in an opposite side wall thereof, and/or a third window 104c formed in a front wall thereof. Windows 104a-104c are configured, dimensioned and located in lower housing portion 104 such that relative displays 157c, 157b and 157d of battery 156 are visible therethrough, when battery 156 is fully inserted in the cavity of lower housing portion 104.

Further, door 105 of surgical device 100 may include a window 105a formed therein such that display 157a of battery 156 is visible through window 105a of door 105 when battery 156 is fully inserted in the cavity of lower housing portion 104 and door 105 properly closed.

It is contemplated that each window 104a-104c, 105a may include a pane of glass or other clear material, as described above, which would provide an end user the ability to see the display(s) of battery 156 therein.

Battery 156 may include a single source of power which is capable of providing power to surgical device 100 to accomplish the surgical procedure, as well as to provide power to any of the displays 157a-157d and/or the speaker 159a. Alternatively, battery 156 may include a primary source of power which is capable of providing power to surgical device 100 to accomplish the surgical procedure, and a secondary source of power which is capable of providing power to any of the displays 157a-157d and/or the speaker 159a.

It is further contemplated that battery 156 and/or surgical device 100 may include an orientation device or sensor 151 (see FIG. 3) or the like, and associated programming, which functions to orient and/or re-orient the images and/or information on each of the displays 157a-157d depending on the orientation of surgical device 100 relative to the end user. Alternatively, the orientation device or sensor 151 and the programming associated therewith can customize the orientation of the images and/or information on the displays 157a-157d such that at least one of the display(s) presents the images and/or information therein in an orientation best suited for viewing by the surgeon, while at least one of the display(s) presents the images and/or information therein in an orientation best suited for viewing by the nurse.

It is contemplated that orientation device or sensor 151 of battery 156 and/or surgical device 100 may include, and are not limited to, linear and/or rotational acceleration sensors which may include accelerometers, magnetometers and/or gyroscopes (linear and/or rotational).

In accordance with the present disclosure, since battery 156 is removed from surgical device 100 prior to any cleaning, sterilizing and/or autoclaving process, it follows that the displays 157a-157d and/or speaker 159a are also removed from surgical device 100 thereby sparing the displays 157a-157d and/or speaker 159a from exposure to the deteriorating nature of the cleaning, sterilizing and/or autoclaving process stemming from the relatively high temperatures and/or pressures and as a result of the chemicals used thereby.

Also in accordance with the present disclosure, when battery 156 is inserted into the cavity of lower housing 104 of surgical device 100, battery 156 is configured to communicate with surgical device 100. In accordance therewith, any information collected by surgical device 100 or stored in surgical device 100 may be displayed on at least one of displays 157a-157d.

By way of example only, displays 157a-157d of battery 156 may display potential failures of surgical device 100, adapter 200 and/or end effector 300, and provide procedural steps for resolving these potential issues; may display, to an end user or sales representative, autoclaving or end of life counts for surgical device 100, adapter 200 and/or end effector 300; and/or may display features of the internal software EEProm; may display battery life.

With reference to FIG. 3, distal half-section 110a of upper housing portion 108 defines a nose or connecting portion 108a. A nose cone 114 is supported on nose portion 108a of upper housing portion 108. Nose cone 114 is fabricated from a transparent material. An illumination member 116 is disposed within nose cone 114 such that illumination member 116 is visible therethrough. Illumination member 116 is in the form of a light emitting diode printed circuit board (LED PCB). Illumination member 116 is configured to illuminate multiple colors with a specific color pattern being associated with a unique discrete event.

Upper housing portion 108 of handle housing 102 provides a housing in which drive mechanism 160 is situated. Drive mechanism 160 is configured to drive shafts and/or gear components in order to perform the various operations of surgical device 100. In particular, drive mechanism 160 is configured to drive shafts and/or gear components in order to selectively move tool assembly 304 of end effector 300 (see FIG. 1) relative to proximal body portion 302 of end effector 300, to rotate end effector 300 about a longitudinal axis "X" (see FIG. 3) relative to handle housing 102, to move anvil assembly 306 relative to cartridge assembly 308 of end effector 300, and/or to fire a stapling and cutting cartridge within cartridge assembly 308 of end effector 300.

As illustrated in FIGS. 1-4, and as mentioned above, distal half-section 110a of upper housing portion 108 defines a connecting portion 108a configured to accept a corresponding drive coupling assembly 210 of adapter 200.

When adapter 200 is mated to surgical device 100, rotatable drive connectors (not shown) of surgical device 100 couple with a corresponding rotatable connector sleeve (not shown) of adapter 200. In this regard, the interface between corresponding drive connectors and connector sleeves are keyed such that rotation of each of drive connector of surgical device 100 causes a corresponding rotation of the corresponding connector sleeve of adapter 200.

The mating of the drive connectors of surgical device 100 with connector sleeves of adapter 200 allows rotational forces to be independently transmitted via each of the respective connector interfaces. The drive connectors of surgical device 100 are configured to be independently rotated by drive mechanism 160. Since each of the drive connectors of surgical device 100 has a keyed and/or substantially non-rotatable interface with the respective connector sleeves of adapter 200, when adapter 200 is coupled to surgical device 100, rotational force(s) are selectively transferred from drive mechanism 160 of surgical device 100 to adapter 200.

The selective rotation of the drive connector(s) of surgical device 100 allows surgical device 100 to selectively actuate different functions of end effector 300. Selective and independent rotation of a first drive connector of surgical device 100 may correspond to the selective and independent opening and closing of tool assembly 304 of end effector 300, and a driving of a stapling/cutting component of tool assembly 304 of end effector 300. Also, the selective and independent rotation of a second drive connector of surgical device 100 may correspond to the selective and independent articulation of tool assembly 304 of end effector 300 transverse to longitudinal axis "X" (see FIG. 3). Additionally, the selective and independent rotation of a third drive connector of surgical device 100 may correspond to the selective and independent rotation of end effector 300 about longitudinal axis "X" (see FIG. 3) relative to handle housing 102 of surgical device 100.

As illustrated in FIG. 1, the end effector is designated as 300. End effector 300 is configured and dimensioned for endoscopic insertion through a cannula, trocar or the like. In particular, in the embodiment illustrated in FIG. 1, end effector 300 may pass through a cannula or trocar when end effector 300 is in a closed condition. End effector 300 includes a proximal body portion 302 and a tool assembly 304. Proximal body portion 302 is releasably attached to a distal coupling 230 of adapter 200 and tool assembly 304 is pivotally attached to a distal end of proximal body portion 302. Tool assembly 304 includes an anvil assembly 306 and a cartridge assembly 308. Cartridge assembly 308 is pivotal in relation to anvil assembly 306 and is movable between an open or unclamped position and a closed or clamped position for insertion through a cannula of a trocar.

Reference may be made to U.S. patent application Ser. No. 13/484,975, filed on May 31, 2012, entitled "HAND-HELD SURGICAL HANDLE ASSEMBLY, SURGICAL ADAPTERS FOR USE BETWEEN SURGICAL HANDLE ASSEMBLY AND SURGICAL END EFFECTORS, AND METHODS OF USE" for a detailed discussion of the construction and operation of surgical device 100.

Reference may be made to U.S. Patent Publication No. 2009/0314821, filed on Aug. 31, 2009, entitled "TOOL ASSEMBLY FOR A SURGICAL STAPLING DEVICE" for a detailed discussion of the construction and operation of end effector 300.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. An electromechanical surgical system, comprising:
a hand-held surgical device, including:
a device housing defining a connecting portion for selectively connecting with an adapter assembly, the housing being configured to removably receive a battery therein, wherein at least a portion of the device housing is transparent;
at least one drive motor supported in the device housing and being configured to rotate at least one rotatable drive shaft; and
a circuit board disposed within the housing for controlling power delivered from a battery to the at least one drive motor;
a battery configured for disposition in the device housing, the battery being capable of powering the at least one drive motor; and
at least one display integral to the battery, wherein the at least one display is configured to display at least one parameter of the surgical device and the device housing is configured such that the at least one display of the battery is visible therethrough, wherein the at least one display of the battery includes multiple displays visible through the transparent portion of the device housing when the battery is received in the device housing.

2. The electromechanical surgical system according to claim 1, further comprising a door supported on the device housing, wherein the door has an open position for permitting insertion of the battery into the device housing and a closed position for retaining the battery in the device housing, wherein at least a portion of the door is transparent, and wherein the at least one display of the battery is visible through the transparent portion of the door when the battery is received in the device housing.

3. The electromechanical surgical system according to claim 1, further comprising a door supported on the device housing, wherein the door has an open position for permitting insertion of the battery into the device housing and a closed position for retaining the battery in the device housing, wherein at least a portion of the door is transparent, and wherein the at least one display of the battery is visible through the transparent portion of the door when the battery is received in the device housing.

4. The electromechanical surgical system according to claim 1, wherein each of the displays of the battery is visible through the device housing.

5. The electromechanical surgical system according to claim 1, wherein at least a portion of the device housing defines a window, and wherein the at least one display of the battery is visible through the window of the device housing when the battery is received in the device housing.

6. The electromechanical surgical system according to claim 5, further comprising a door supported on the device housing, wherein the door has an open position for permitting insertion of the battery into the device housing and a closed position for retaining the battery in the device housing, wherein the door defines a window, and wherein the at least one display of the battery is visible through the window of the door when the battery is received in the device housing.

7. The electromechanical surgical system according to claim 1, further comprising a door supported on the device housing, wherein the door has an open position for permitting insertion of the battery into the device housing and a closed position for retaining the battery in the device housing, wherein the door defines a window, and wherein the at least one display of the battery is visible through the window of the door when the battery is received in the device housing.

8. The electromechanical surgical system according to claim 1, wherein the device housing includes multiple windows, and wherein each of the displays of the battery is visible through a respective window of the device housing.

9. The electromechanical surgical system according to claim 1, wherein the battery includes a speaker integrally formed therewith.

10. The electromechanical surgical system according to claim 1, further comprising:
an end effector configured to perform at least one function, the end effector including at least one axially translatable drive member; and
an adapter assembly for selectively interconnecting the end effector and the surgical device, the adapter assembly including:
an adapter housing configured and adapted for selective connection to the connecting portion of the surgical device and to be in operative communication with each of the at least one rotatable drive shaft of the surgical device;
an outer tube having a proximal end supported by the adapter housing and a distal end configured and adapted for connection with the end effector, wherein the distal end of the outer tube is in operative communication with each of the at least one axially translatable drive member of the end effector;
at least one drive converter assembly for interconnecting a respective one of the at least one rotatable drive shaft of the surgical device and one of the at least one axially translatable drive member of the end effector, wherein the at least one drive converter assembly includes a first end that is connectable to a drive shaft of the surgical device and a second end that is connectable to the at least one axially translatable drive member of the end effector, wherein the at least one drive converter assembly converts and transmits a rotation of the rotatable drive shaft of the surgical device to an axial translation of the at least one axially translatable drive member of the end effector.

11. The electromechanical surgical system according to claim 10, wherein at least one of the displays of the battery displays at least one of potential failures of at least one of the battery, the surgical device, the adapter and the end effector; procedural steps for resolving the potential failures; autoclaving counts for at least one of the surgical device, the adapter and the end effector; end of life counts for at least one of the battery, the surgical device, the adapter and the end effector; features of an internal software EEProm of the surgical device, and battery life.

12. The electromechanical surgical system according to claim 1, wherein the at least one displayed parameter of the surgical device is selected from a group consisting of potential failures of the surgical device, procedural steps resolving the potential failures, autoclaving counts for the surgical device, end of life counts for the surgical device, and features of an internal software EEProm.

13. The electromechanical surgical system according to claim 12, wherein the at least one display of the battery displays multiple parameters of the surgical device.

14. The electromechanical surgical system according to claim 1, wherein the device housing is transparent, and wherein the at least one display of the battery is visible through the device housing when the battery is received in the device housing.

15. An electromechanical surgical system, comprising:
a hand-held surgical device, including:
a device housing defining a connecting portion for selectively connecting with an adapter assembly, the housing being configured to removably receive a battery therein;
at least one drive motor supported in the device housing and being configured to rotate at least one rotatable drive shaft; and
a circuit board disposed within the housing for controlling power delivered from a battery to the at least one drive motor;
a battery configured for disposition in the device housing, the battery being capable of powering the at least one drive motor; and
at least one display integral to the battery, wherein the at least one display is configured to display at least one parameter of the surgical device and the device housing is configured such that the at least one display of the battery is visible therethrough, wherein at least one of the surgical device or the battery includes an orientation device configured to change an orientation of an image displayed on the at least one display depending on a particular orientation of the surgical device.

16. The electromechanical surgical system according to claim 15, wherein the orientation device includes at least one of a linear acceleration sensor, a rotational acceleration sensor, a magnetometer, a linear gyroscope and a rotational gyroscope.

17. A battery for use in a hand-held electromechanical surgical device, the battery comprising:
a primary source of energy for energizing the hand-held electromechanical surgical device;
at least one display integral to the battery for displaying a parameter of the battery and the surgical device; and an orientation device configured to change an orientation of an image displayed on the at least one display depending on a particular orientation of the battery.

18. The battery according to claim 17, wherein the battery is configured to display at least one of potential failures of at least one of the battery and the surgical device; procedural steps for resolving the potential failures; end of life counts for at least one of the battery and the surgical device; features of an internal software EEProm of the surgical device.

* * * * *